United States Patent
Nabulsi

[11] Patent Number: 5,918,281
[45] Date of Patent: Jun. 29, 1999

[54] PERSONAL SPEEDOMETER

[76] Inventor: Haz Nabulsi, 1075 E. Rose Cir., Los Altos, Calif. 94024

[21] Appl. No.: 08/653,919

[22] Filed: May 28, 1996

[51] Int. Cl.$^6$ .................................................. G01N 29/02
[52] U.S. Cl. ........................................... 73/597; 73/861.28
[58] Field of Search ................................. 73/597, 861.27, 73/861.28, 861.29; 367/90, 91

[56] References Cited

U.S. PATENT DOCUMENTS

| | | | |
|---|---|---|---|
| 3,898,878 | 8/1975 | Stallworth et al. | 73/181 |
| 4,011,753 | 3/1977 | Hausler | 73/194 A |
| 4,028,938 | 6/1977 | Eck | 73/194 A |
| 4,337,667 | 7/1982 | Takada | 73/861.28 |
| 4,372,166 | 2/1983 | Loveland | 73/861.28 |
| 4,483,202 | 11/1984 | Ogura et al. | 73/861.27 |
| 4,488,428 | 12/1984 | Taniuchi | 73/861.27 |
| 4,506,353 | 3/1985 | Rott et al. | 367/91 |
| 4,633,719 | 1/1987 | Vander Heyden | 73/861.28 |
| 4,685,093 | 8/1987 | Gill | 367/89 |
| 4,728,954 | 3/1988 | Phelan et al. | 342/115 |
| 4,757,714 | 7/1988 | Purdy et al. | 73/597 |
| 4,860,593 | 8/1989 | de Concini et al. | 73/861.29 |
| 4,885,942 | 12/1989 | Magori | 73/861.28 |
| 4,914,638 | 4/1990 | Milner | 367/90 |

*Primary Examiner*—Michael Brock
*Assistant Examiner*—Nashmiya Ashraf
*Attorney, Agent, or Firm*—Skjerven, Morrill, MacPherson, Franklin & Friel LLP; Serge J. Hodgson

[57] ABSTRACT

The speed of an object is measured using a device which includes a transmitter spaced a predetermined distance from a receiver. A first sound wave is propagated through air with a first velocity, typically zero velocity. A second sound wave is propagated through air, the air having a second velocity which approximately equals the air speed of the object. The difference in time between the two sound waves reaching the receiver is measured and used to calculate the air speed of the object, which is then displayed to the user. The device is readily mounted on a pair of glasses wherein the user can read the displayed air speed without involving the user's hands.

8 Claims, 9 Drawing Sheets

PERSONAL SPEEDOMETER

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates generally to speedometers and in particular to a speedometer which can be worn by a person to measure the air speed of the person as the person engages in an event such as skiing, skating or horseback riding.

BACKGROUND OF THE INVENTION

Several systems use ultrasonic sound waves to measure the velocity of a fluid through a conduit. In Takada, U.S. Pat. No. 4,337,667, an ultrasonic flowmeter is disclosed which uses a phase difference method to calculate the velocity of a fluid through a conduit. The ultrasound flow rate meter includes a single transmitter for transmitting a continuous ultrasonic wave into a fluid flowing through a conduit and a single receiver spaced a predetermined distance from the transmitter for receiving the ultrasonic wave. The phase difference between the signals at the transmission point and the reception point is measured and used to calculate the velocity of the fluid in the conduit.

One disadvantage of the prior art ultrasonic flowmeters is that compensation for temperature changes in the fluid is not provided. Compensation for temperature changes is needed because the speed at which the ultrasonic wave propagates through the fluid, and hence the phase of the signal at the reception point, is related to the temperature of the fluid. Since the phase of the signal at the reception point is used to calculate the velocity of the fluid in the conduit, temperature changes in the fluid result in erroneous changes in the measured velocity of the fluid.

Another disadvantage of the prior art ultrasonic flowmeters is that long conduits are necessary to accurately measure the fluid velocity. This is because ultrasonic sound waves reflected from the ends of the conduit become significant as the ends of the conduit are brought closer to the receiver. (The effective soundwave at the receiver is the vector sum of the soundwave transmitted from the transmitter and the reflected sound waves.)

It is desirable to have a device for measuring the air speed of an object, in particular when conventional ground speed calculations are impractical. Examples include sporting and recreational activities such as skiing and horseback riding. To accommodate such uses, it is important that the device is small, lightweight and is able to operate for an extended period of time with a minimum amount of power consumption. It is also important that the device accurately measures air speed over a wide variety of temperatures.

SUMMARY OF THE INVENTION

In accordance with this invention, a device for measuring the air speed of an object includes a tube through which air can flow wherein the air velocity through the tube approximately equals the air speed of the object. Thus the air speed of the object can be accurately measured by accurately measuring the air velocity in the tube.

The device includes a transmitter and receiver mounted in the tube a predetermined distance apart. Air flows through the tube from the transmitter to the receiver. The transmitter generates sound waves having a fixed frequency which propagate through the air in the tube to the receiver. When the air velocity in the tube increases, the travel time of sound waves from the transmitter to the receiver decreases (increases) if the receiver is located downstream (upstream) from the transmitter. As a result of the shorter travel time, the phase of the sound wave at the receiver changes from what it would have been with no air velocity in the tube. By measuring the change in phase from a sound wave propagated the same distance through air moving with a reference velocity (typically zero velocity), and knowing the distance between the transmitter and the receiver, the air velocity can be accurately calculated. The calculated air velocity is then displayed as the air speed of the object.

In some embodiments, a thermistor is included which compensates for changes in the speed of sound associated with changes in air temperature, thus increasing the accuracy of the device.

In some embodiments, the device is mounted on a pair of glasses worn by the user. The display is mounted so as not to block the user's normal field of vision. A magnifying lens is located between the user's eye and the display. The user can read the displayed air speed by looking towards the direction where the display is mounted. This allows the user to readily read the air speed without involving the user's hands.

In an alternative embodiment, air flow creates a force which moves a plate. Mechanical linkage transfers the plate movement to a speed dial, which displays the plate movement as air speed.

In another embodiment, air flow-causes a turbine to rotate. The turbine is connected to an electric motor which produces an AC signal with a frequency corresponding to the speed at which the turbine rotates. A pulse counter counts the cycles of the AC signal produced by the electric motor and outputs the count to a controller. The controller calculates the speed of the air flow (and hence the air speed of the user or object) from the cycle count and outputs that air speed to a display.

In an alternative embodiment, a satellite global position system (GPS) is used to determine the distance the object has moved over a fixed period of time. The ground speed of the object is then readily calculated.

DESCRIPTION OF THE PREFERRED EMBODIMENTS

Figure 1:
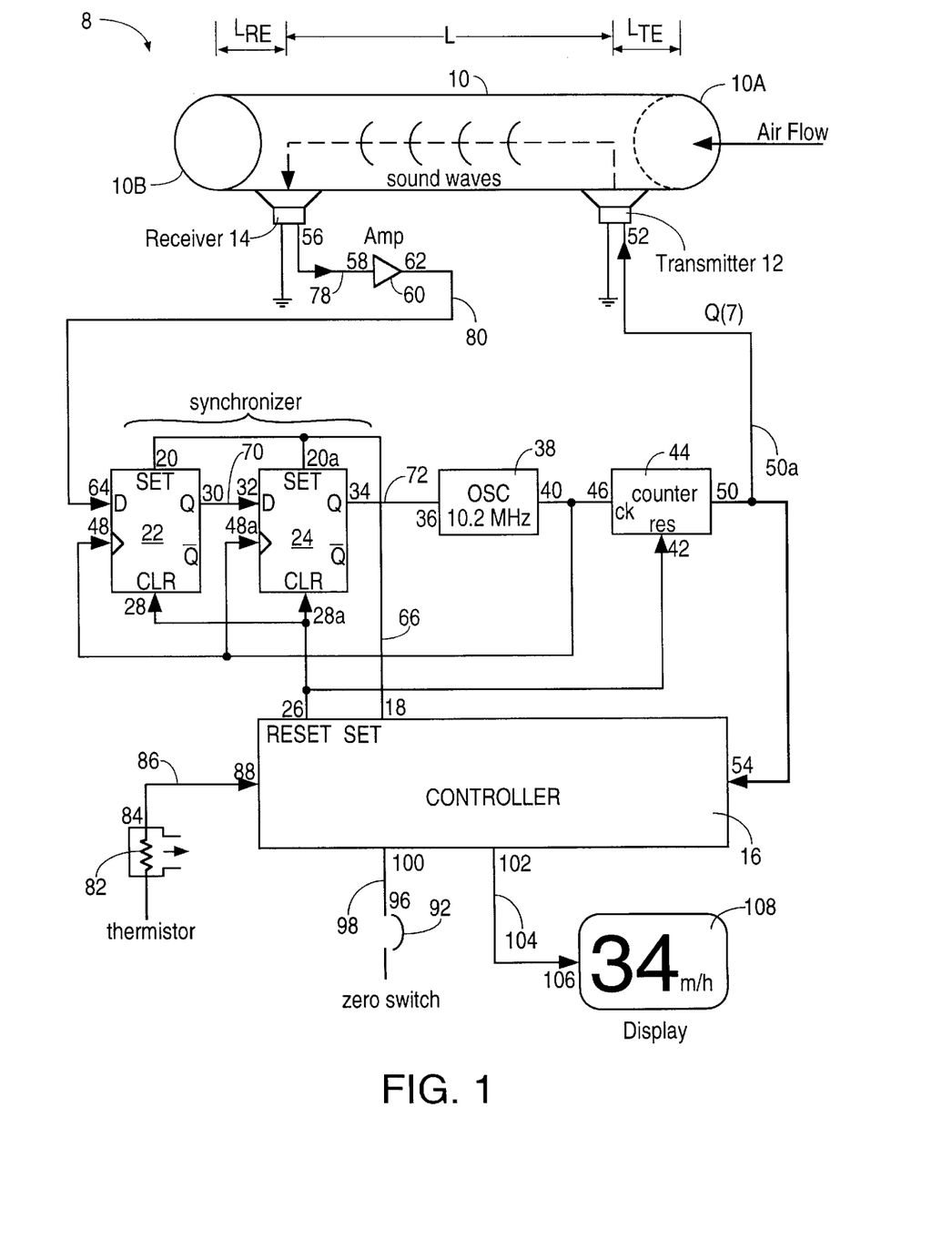
FIG. 1 is a block diagram of one embodiment of the personal speedometer in accordance with the present invention.

FIG. 1 is a block diagram of an apparatus 8 of one embodiment of the invention. As shown in FIG. 1, apparatus 8 includes a hollow tube 10 through which air can flow. A transmitter 12 and a receiver 14 are positioned along tube 10 at a fixed distance apart shown as a distance L. As further shown in FIG. 1, transmitter 12 and receiver 14 are positioned at distances $L_{TE}$, $L_{RE}$ from the tube ends 10A, 10B, respectively.

An ultrasonic sound wave transmitted from transmitter 12 travels through air in tube 10 over the distance L to receiver 14. The speed at which the sound wave travels from transmitter 12 to receiver 14, over the distance L, is related to the velocity of air flow through tube 10. When air in tube 10 is traveling at a reference velocity, the sound wave travels the distance L at a speed $V_{REF}$ (equal to the speed of sound in air if the reference velocity is zero) and within a time $T_{REF}$, as set forth in the following equation:

$$V_{REF} = L/T_{REF} \tag{1}$$

However, when air is moving at a speed V in tube 10 in the direction shown from transmitter 12 to receiver 14, the sound wave travels the distance L faster (at speed V2) due to the increase in speed associated with the air flow. This increase in speed is set forth in the following equation:

$$V2 = V + V_{REF} \tag{2}$$

Since the signal travels faster at speed V2, the signal travels distance L in a shorter time T2 according to the following equation:

$$V2 = L/T2 \tag{3}$$

The difference T in travel time for the signal to travel from the transmitter to receiver at speed V2 versus $V_{REF}$ is set forth in the following equation:

$$T = T_{REF} - T2 \tag{4}$$

The speed of air flow V can be derived using equations 1 to 4 as follows:

$$\begin{aligned}
V = V2 - V_{REF} &= L/T2 - L/T_{REF} \\
&= L\left(\frac{1}{T2} - \frac{1}{T_{ref}}\right) \\
&= L\left(\frac{1}{T_{ref} - T} - \frac{1}{\left(\frac{L}{V_{ref}}\right)}\right) \\
V &= L\left(\frac{1}{\left(\frac{L}{V_{ref}}\right) - T} - \frac{V_{ref}}{L}\right)
\end{aligned} \tag{5}$$

As set forth in equation (5), speed V can be calculated if T and $V_{REF}$ are determined, L having a known and fixed value. If $V_{REF}$ equals the speed of sound in air, 1136 feet/second at 25° C., (which occurs when air in the tube is not moving), then speed V (which will always be higher than $V_{REF}$ when air is moving from the transmitter to the receiver) can be determined from equation 5 by measuring T and using the known values of L, $V_{REF}$.

Figure 2:
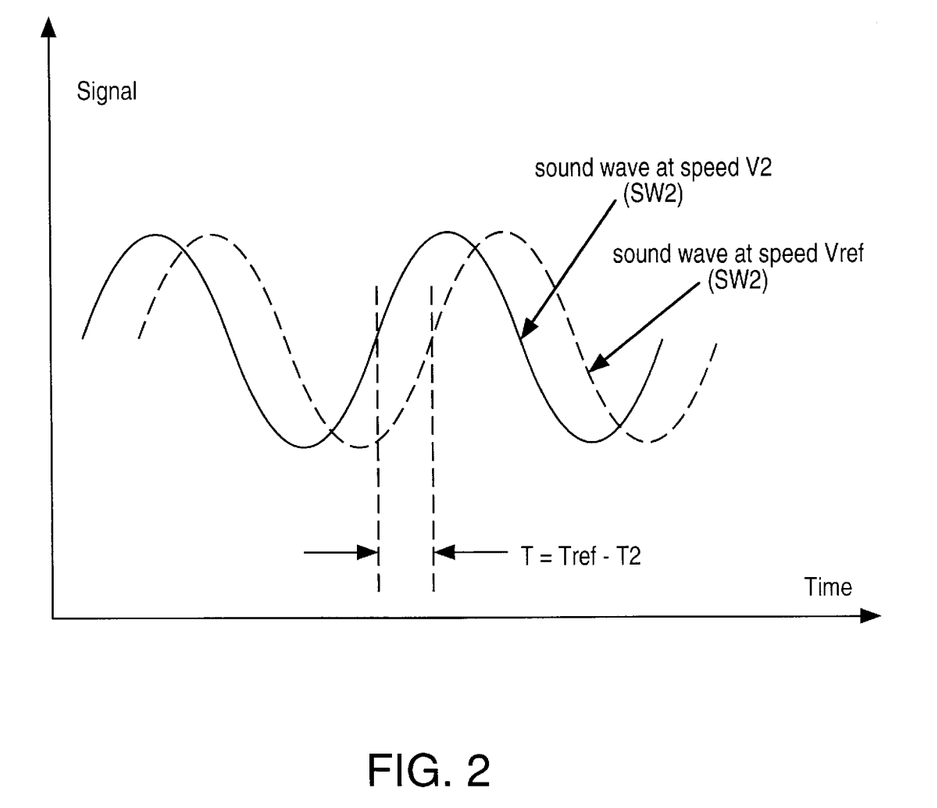
FIG. 2 is a graph which illustrates the waveforms of sound waves traveling at various speeds in accordance with the present invention.

FIG. 2 shows waveforms of sound waves received at receiver 14 traveling at speed $V_{REF}$ and V2, respectively. As shown in FIG. 2, the sound wave traveling at speed V2 (sound wave $SW_2$) shall be out of phase with the sound wave traveling at $V_{REF}$ (sound wave $SW_{REF}$). Since sound wave $SW_2$ travels the distance L to receiver 14 in less time than sound wave $SW_{REF}$ sound wave $SW_2$ will have gone through fewer cycles than sound wave $SW_{REF}$ in the time required for sound wave $SW_2$ to travel from the transmitter to the receiver because sound waves $SW_2$, $SW_{REF}$ have the same frequency. Since sound wave $SW_2$ has gone through fewer cycles than sound wave $SW_{REF}$, sound waves $SW_2$, $SW_{REF}$ shall be out of phase when received at receiver 14. The difference in phase is directly related to T. Thus by measuring the phase difference, T can be readily determined allowing V to be calculated from equation 5.

Referring back to FIG. 1, apparatus 8 includes a controller 16 having a first output lead 18 coupled by a conductor 66 to "set" input lead 20 of a first synchronizing flip flop 22 and to "set" input lead 20a of a second synchronizing flip flop 24. (Flip flop 24 shields the system from a potential "meta stable" output signal from flip flop 22.) Controller 16 "sets" flip-flops 22, 24 by asserting a "set" signal on conductor 66. Controller 16 has a second output lead 26 coupled to a reset ("res") input lead 42 of a counter 44 and to clear ("clr") input leads 28, 28a of flip flops 22, 24, respectively. Controller 16 resets counter 44 and "clears" flip-flops 22, 24 by asserting a reset signal on output lead 26.

A first output lead 30 from flip-flop 22 is coupled to input lead 32 of flip-flop 24 by a conductor 70. A first output lead 34 from flip-flop 24 is coupled by conductor 72 to input lead 36 of a 10.2 Mega-hertz (MHz) oscillator 38. The signal asserted by flip-flop 24 on conductor 72 controls the on-off operation of oscillator 38.

Output lead 40 from oscillator 38 is coupled to input lead 46 of counter 44. Counter 44 receives a 10.2 MHz signal on input lead 46 when oscillator 38 is operating. Output lead 40 is also coupled to input leads 48 and 48a of flip-flops 22, 24, respectively. Input leads 48 and 48a receive clock signals for flip-flops 22, 24, respectively.

Counter 44 has an output bus 50 comprising an eight (8) bit bus representing output stages (Q7 through Q0) of counter 44. All eight (8) channels of output bus 50 are coupled to an input port 54 of controller 16. Input port 54 of controller 16 is eight (8) bits wide. Counter 44 sends count information discussed below to controller 16 at input port 54. The most significant bit (Q7) on output bus 50 is also transmitted to a first input lead 52 of transmitter 12 on lead 50a.

Counter 44 has an eight stage divider which divides down the 10.2 MHz signal received from oscillator 38 by 256. Thus, counter 44 outputs a signal on the lead 50a carrying the most significant bit (Q7) on output bus 50 which has a frequency approximately equal to 40 kilohertz (KHz) when oscillator 38 is operating. Transmitter 12 generates a 40 KHz sound wave from the 40 KHz signal received on lead 50a at input lead 52. The 40 KHz sound wave propagates through air in tube 10 and is received by receiver 14.

Receiver 14 has a first output lead 56 coupled by a conductor 78 to input lead 58 of amplifier 60. Amplifier 60 has an output lead 62 coupled by a conductor 80 to D input lead 64 of flip-flop 22. Receiver 14 generates a 40 KHz signal on conductor 78 from the received 40 KHz sound wave. Amplifier 60 amplifies and shapes the signal received on conductor 78 and outputs the amplified and shaped signal on conductor 80.

A zero switch 92 has an output lead 96 coupled by conductor 98 to input port 100 of controller 16. The operation of zero switch 92 is described below along with the operation of apparatus 8.

A display 108 has an input lead 106 coupled by a conductor 104 to output lead 102 of controller 16. The display is preferably a conventional liquid crystal display (LCD) which displays the air speed V numerically according to the output signal from controller 16 received on conductor 104. Alternative embodiments of the present invention use a light emitting diode (LED) display. Other embodiments use a mechanical dial with a needle pointer as a display or a speaker to broadcast the air speed to the user.

Figure 3:
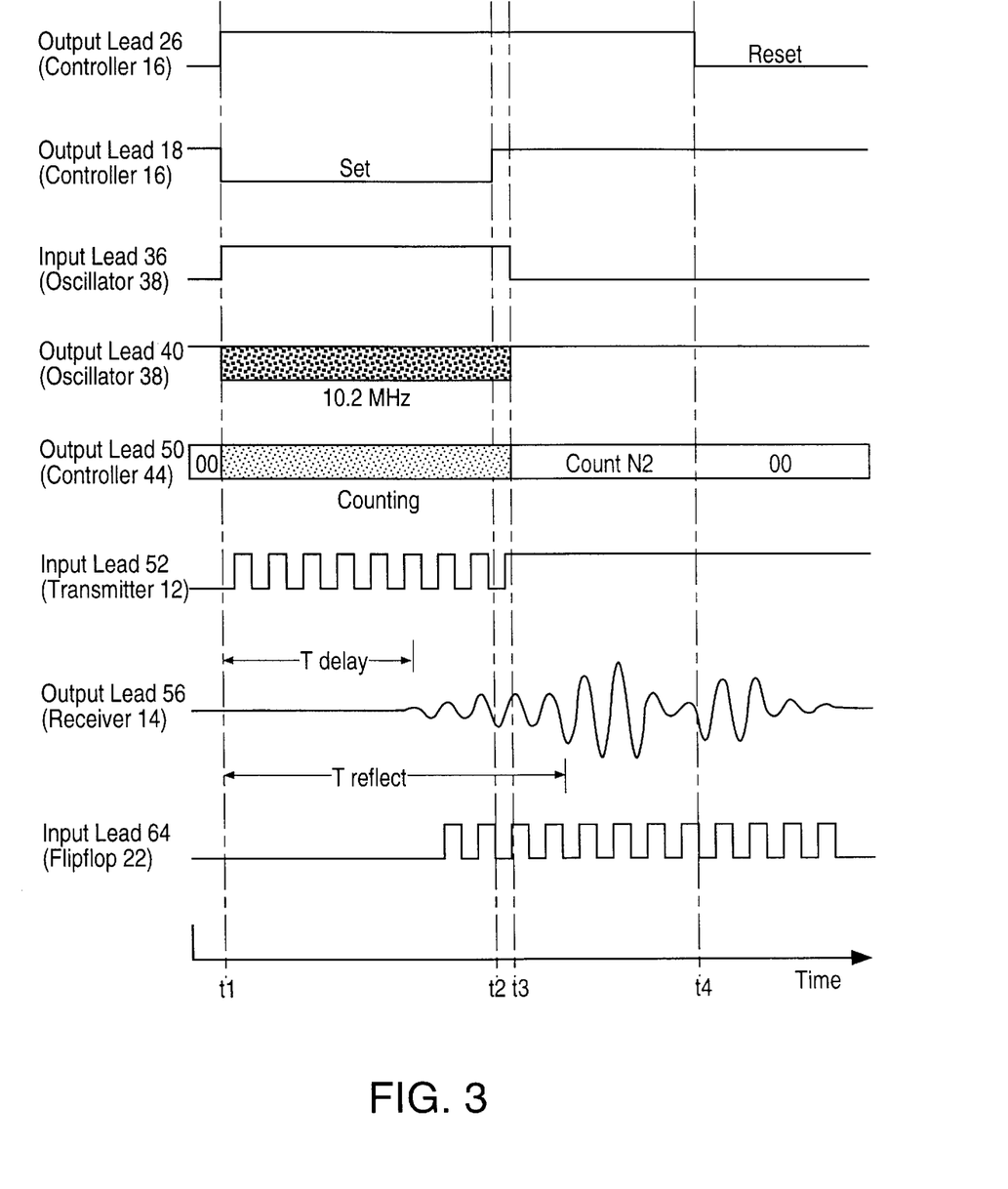
FIG. 3 is a timing diagram which illustrates waveforms at various leads of the block diagram of FIG. 1 during a measurement cycle in accordance with the present invention.

Referring to the timing diagram of FIG. 3 and the block diagram of FIG. 1, initially controller 16 is asserting a reset signal (logic low) at output lead 26. The reset signal is received by counter 44 at input lead 42 which resets counter 44 to zero (counter 44 outputs 00 at output lead 50) in response thereto. The reset signal is also received at input leads 28, 28a of flip-flops 22, 24, respectively, which "clears" flip-flops 22, 24, i.e. flip-flop 24 outputs a logic low signal at output lead 34 to input lead 36 of oscillator 38. Since oscillator 38 does not operate until it receives a logic high signal at input lead 36, oscillator 38 does not output a 10.2 MHz signal at output lead 40.

At time t1, controller 16 de-asserts the reset signal output at output lead 26 (the signal at output lead 26 goes from logic low to logic high) and asserts the SET signal at output lead 18 (the signal at output lead 18 goes from logic high to logic low). The SET signal is received via conductor 66 at input leads 20, 20a of flip-flops 22, 24, respectively which "sets" flip-flops 22, 24, i.e. flip-flop 24 outputs a logic high signal at output lead 34 to input lead 36 of oscillator 38.

As a result, oscillator 38 outputs a 10.2 MHz signal on output lead 40. The 10.2 MHz signal is received at clock input leads 48, 48a of flip-flops 22, 24 respectively. However, flip-flops 22, 24 are unaffected by the signal received at clock input leads 48, 48a and remain set since controller 16 is still asserting the SET signal at output lead 18. Counter 44 also receives the 10.2 MHz signal at input lead 46. Counter 44 divides down the 10.2 MHz signal to approximately 40 KHz and outputs the 40 KHz signal on lead 50a which carries the most significant bit Q7 on output bus 50.

Counter 44 is also counting and outputting the count information at output bus 50. (Counter 44 counts from 0–256 and overflows several times, i.e. counts from 0–256 several times. This count information is disregarded by controller 16).

Transmitter 12 receives the 40 KHz signal at input lead 52 and transmits a 40 KHz sound wave. The 40 Khz sound wave propagates through air in tube 10 where it is received by receiver 14.

Receiver 14 outputs a 40 KHz signal (having a periodicity equal to the periodicity of the received soundwave) at output lead 56 which is received at input lead 58 of amplifier 60. Amplifier 60 amplifies and shapes the 40 KHz signal received at input lead 58 and sends this amplified and shaped signal on output lead 62 to input lead 64 of flip-flop 22. However, the received signal at input lead 64 does not toggle flip-flop 22 because it remains set since controller 16 is still asserting the SET signal at output lead 18. Controller 16 continues to assert the SET signal until, at a time t2, controller 16 de-asserts the SET signal.

Of importance, the amount of time between t1 and t2 has a predetermined and precise value. As shown by the signal waveform at output lead 56, there is a time period $T_{delay}$ between time t1 of the transmission of the ultrasonic soundwave by transmitter 12 and the time of reception of the ultrasonic soundwave by receiver 14. $T_{delay}$, at a minimum, is the amount of time required for the ultrasonic sound wave to travel the distance L from transmitter 12 to receiver 14. Thus the amount of time between t1 and t2 must be greater than or equal to $T_{delay}$.

As further shown in FIG. 3, after a time period $T_{reflect}$, soundwaves reflected from ends 10A, 10B (see FIG. 1) interfere with the unreflected soundwave transmitted by transmitter 12 and received by receiver 14. $T_{reflect}$ is the amount of time required for the ultrasonic wave to travel from transmitter 12 to end 10A or end 10B and to receiver 14. The reflected soundwaves change the amplitude and phase of the received soundwave and hence result in erroneous air flow velocity calculation if measured (the effective soundwave at receiver 14 is the vector sum of the unreflected soundwave transmitted by transmitter 12 and the reflected soundwaves.) Thus the amount of time between t1 and t2 should be less than $T_{reflect}$.

Distances L, $L_{TE}$ and $L_{RE}$ (see FIG. 1) determine $T_{delay}$ and $T_{reflect}$. In one embodiment, L is four inches, $L_{TE}$ is one inch and $L_{RE}$ is one inch. In this embodiment, $T_{delay}$ is approximately equal to 300 microseconds ($\mu$sec), $T_{reflect}$ is approximately equal to 450 $\mu$sec and the amount of time between t1 and t2 is in the range of 300 $\mu$sec to 450 $\mu$sec, and preferably is 375 $\mu$sec.

At time t2, controller 16 de-asserts the SET signal on output lead 18 (the signal on output lead 18 goes from logic low to logic high). Flip-flops 22, 24 receive the 10.2 MHz signal generated by oscillator 38 at input leads 48, 48a. As discussed above, the signal received at input lead 64 of flip-flop 22 is a 40 Khz signal. Thus for every cycle of the signal at input lead 64, flip-flop 22 has read the signal at input lead 64 approximately two hundred and fifty six times. This enables flip-flop 22 to toggle, i.e. the signal output on output lead 30 will go from logic high to logic low, precisely when the signal at input lead 64 goes from low to high on its next wave transition. This logic low signal is then received on input lead 32 of flip-flop 24 via conductor 70. Clock input lead 48a of flip-flop 24 is also receiving a 10.2 MHz signal. Thus flip-flop 24 will toggle on the next low-to-high transition of the 10.2 MHz signal. When flip-flop 24 toggles, a logic low signal is output on conductor 72 from output lead 34.

Oscillator 38 receives the logic low signal at input lead 36 at time t3. As a result, oscillator 38 stops outputting a 10.2 MHz signal at output lead 40 at time t3. Thus, the signal received at input lead 46 of counter 44 stops, and counter 44 stops counting with a count N2 that, as described below, corresponds directly to time T in equation (5).

At time t4 controller 16 reads the count information at output lead 44 and asserts the reset signal at output lead 26 which clears counter 44 and flip-flops 22, 24.

The velocity of air flow through tube 10 is calculated as follows. Initially, the user pushes zero switch 92 and pulls down to ground the signal at input lead 100. This causes controller 16 to set the circuit by deasserting the reset signal at output lead 26 and asserting the SET signal at output lead 18. This initiates the measurement sequence described above. As a result, a first count $N_{REF}$ is received and stored by controller 16. The measurement sequence is repeated for air flowing through tube 10 with velocity V. As a result, a second count N2 is received by controller 16.

$N_{REF}$ and N2 have count values between 0–256 (counter 44 counts between 0–256). Controller 16 accounts for the spillover of counter 44 by comparing N2 to $N_{REF}$. To illustrate, if N2 is 250 and $N_{REF}$ is 12, controller 16 assigns $N_{REF}$ a value of 268 (256+12). However, if N2 is 250 and $N_{REF}$ is 254, then controller 16 assigns $N_{REF}$ a value of 254.

The difference in counter values N is set forth in the following equation:

$$N = N_{REF} - N2 \quad (6)$$

Since each count of the counter equals 1/(10.24 MHz) (or $9.7 \times 10^{-8}$ second), controller 16 calculates T (in seconds) from the difference in counter values N according to the following equation:

$$T = N * 1/(10.24 * 10^6) \quad (7)$$

Controller 16 then calculates air speed V by substituting the calculated value of T into equation 5. Controller 16 outputs the calculated value of air speed V to display 108, which displays the air speed as the speed of the object.

Controller 16 periodically measures the current air speed and updates the display with the current air speed. Generally, it is desirable to have controller 16 measure the current air speed frequently thus updating the information displayed to the user frequently. However, each air speed measurement consumes a certain amount of power and it is desirable to minimize power consumption. In one embodiment, controller 16 measures the current air speed and updates the display with the current air speed every 0.1 seconds.

The speed with which sound travels through air changes as air temperature changes. To compensate for changes in speed associated with air temperature, one embodiment uses a thermistor (82 in FIG. 1). Thermistor 82 has an output lead 84 coupled by a conductor 86 to a second input lead 88 of controller 16. Thermistor 82 provides a resistance which changes in relation to temperature. Controller 16 measures the resistance and calculates the current air temperature.

Controller 16 uses the measured current air temperature to provide dynamic and static temperature compensation.

In one embodiment, controller 16 provides dynamic temperature compensation by calculating $V_{REF}$ for equation (5) at the current air temperature $T_{current}$ from the following equation:

$$V_{ref} = V_{std} + \left(\frac{\Delta V}{\Delta Temp}\right)(T_{current} - T_{std}) \quad (8)$$

where:

$V_{std}$=velocity of sound through air at a temperature $T_{std}$, $$\left(\frac{\Delta V}{\Delta Temp}\right)$$

the derivative of velocity of sound with respect to air temperature
Since $V_{std}$=1136 ft/sec when $T_{std}$=25° C. and $$\left(\frac{\Delta V}{\Delta Temp}\right) = 2.0\frac{(ft/sec)}{°C.}$$

equation (8) simplifies to $$V_{ref} = 1136\frac{ft}{sec} + \left(\frac{2.0\ ft/sec}{°C.}\right)(T_{current} - 25°\ C.) \quad (9)$$

Using equation (9), controller 16 calculates $V_{REF}$ at the current air temperature for use in equation 5.

Controller 16 also uses the measured current air temperature to provide static temperature compensation. In one embodiment, static temperature compensation is provided by calculating what the counter value of $N_{ref}$ in equation (6) would have been had zero switch 92 been pushed at the current air temperature $T_{current}$ as set forth in the following equations:

$$V_{ref} = \frac{L}{Time_{ref}}$$

$$V_{switch} = \frac{L}{Time_{switch}}$$

where:

$Time_{switch}$, $Time_{ref}$=Time for sound to travel the distance L in still air at the temperature when the switch was pushed ($T_{switch}$) and at the current air temperature ($T_{current}$), respectively.

$V_{switch}$, $V_{ref}$=Velocity of sound in still air at $T_{switch}$, $T_{current}$, respectively (calculated from equation (9)).

$$\begin{aligned}\Delta V = V_{ref} - V_{switch} &= \frac{L}{Time_{ref}} - \frac{L}{Time_{switch}} \quad (10)\\ &= L\left(\frac{1}{Time_{ref}} - \frac{1}{Time_{switch}}\right)\\ &= L\left(\frac{(Time_{switch} - Time_{ref})}{(Time_{ref})(Time_{switch})}\right)\\ &= \frac{L\Delta Time}{\left(\frac{L}{V_{ref}}\right)\left(\frac{L}{V_{switch}}\right)}\\ \Delta V &= \frac{\Delta Time V_{ref} V_{switch}}{L}\end{aligned}$$

where $\Delta$ Time is the difference in time required for sound to travel the distance L at temperatures $T_{current}$, $T_{switch}$. Solving equation (10) for $\Delta$ Time yields $$\Delta Time = \frac{L\Delta V}{V_{ref}V_{switch}}.$$

Since each count of the counter equals $$\frac{1\ second}{10.24 \times 10^6}$$

then the counter correction value $\Delta N$ equals:

$$\Delta N = \Delta Time(10.24 \times 10^6) = \frac{L\Delta V}{V_{ref}V_{switch}}(10.24 \times 10^6)$$

and $$N_{ref} = N_{switch} + \Delta N = N_{switch} + \frac{L\Delta V(10.24 \times 10^6)}{V_{ref}V_{switch}} \quad (11)$$

where:

$N_{ref}$ what the counter value would have been had zero switch 92 been pushed at air temperature $T_{current}$, $N_{switch}$=the actual counter value obtained when zero switch 92 was pushed.

$N_{ref}$ is then calculated by substituting the known values of L and $N_{switch}$ and the calculated values of $\Delta V$, $V_{ref}$, $V_{switch}$ into equation 11.

Figure 4:
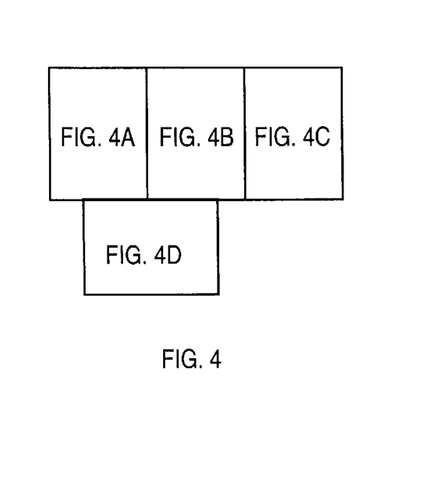
FIG. 4 which consists of FIGS. 4A, 4B, 4C and 4D is a schematic diagram of one embodiment of a personal speedometer in accordance with the present invention.
Figure 4A:
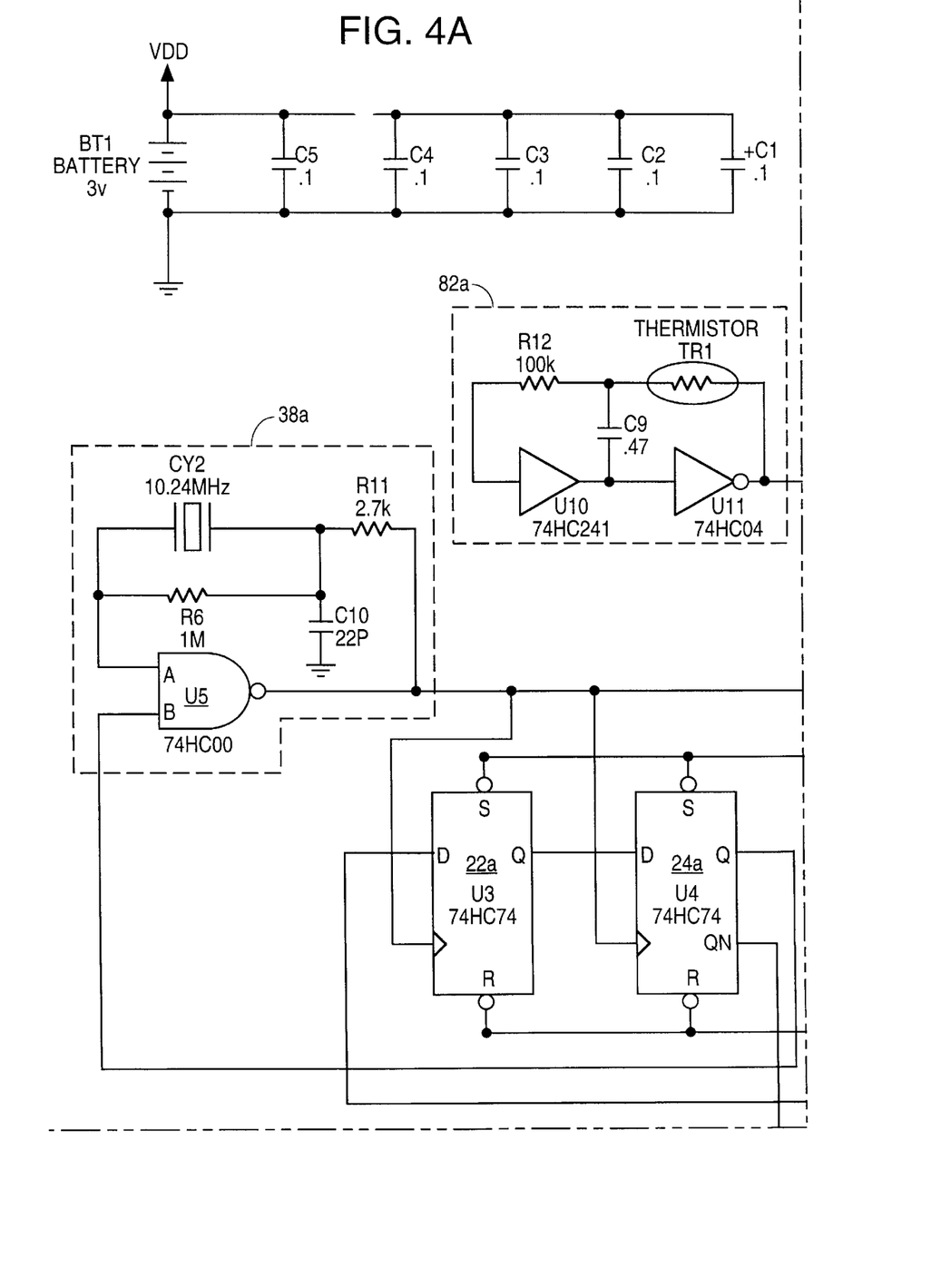
Figure 4B:
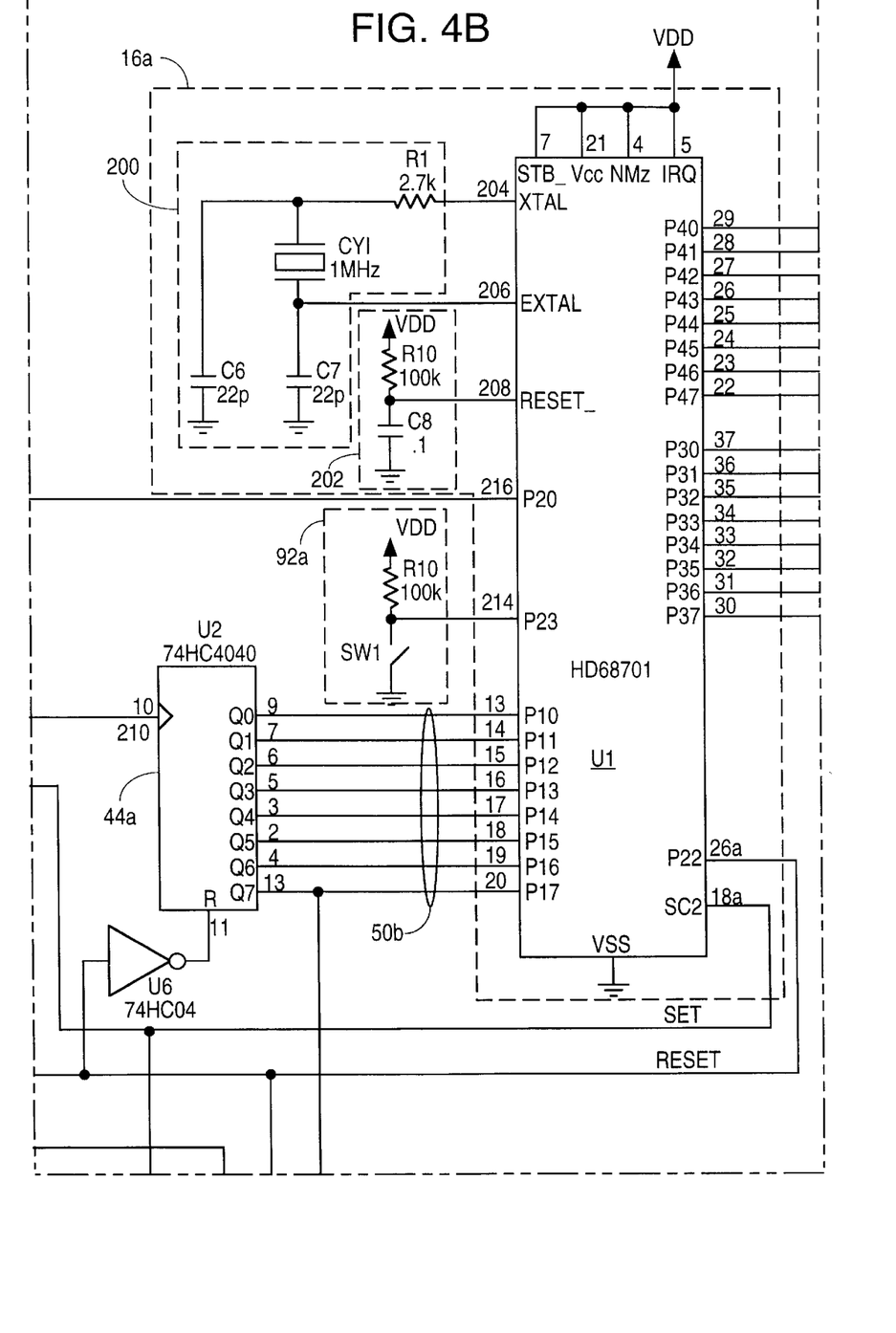
Figure 4C:
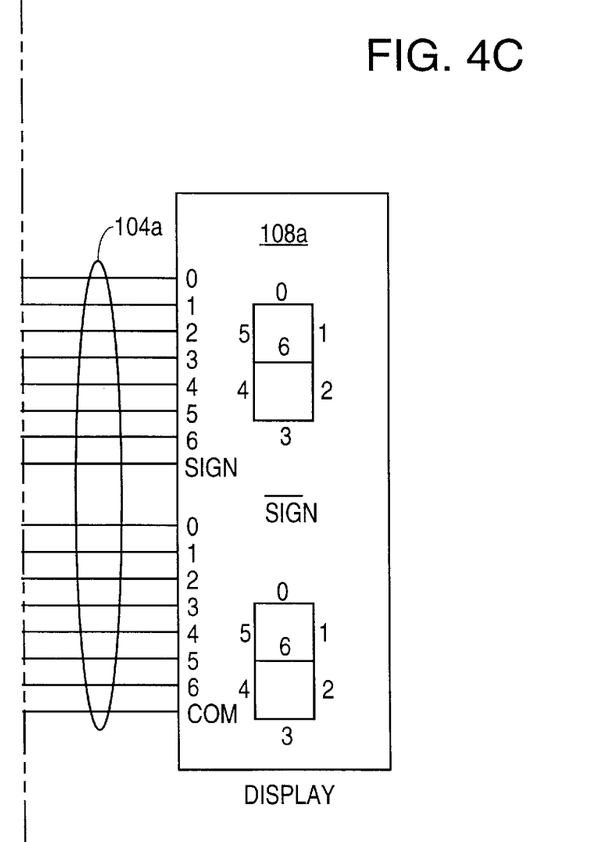
Figure 4D:
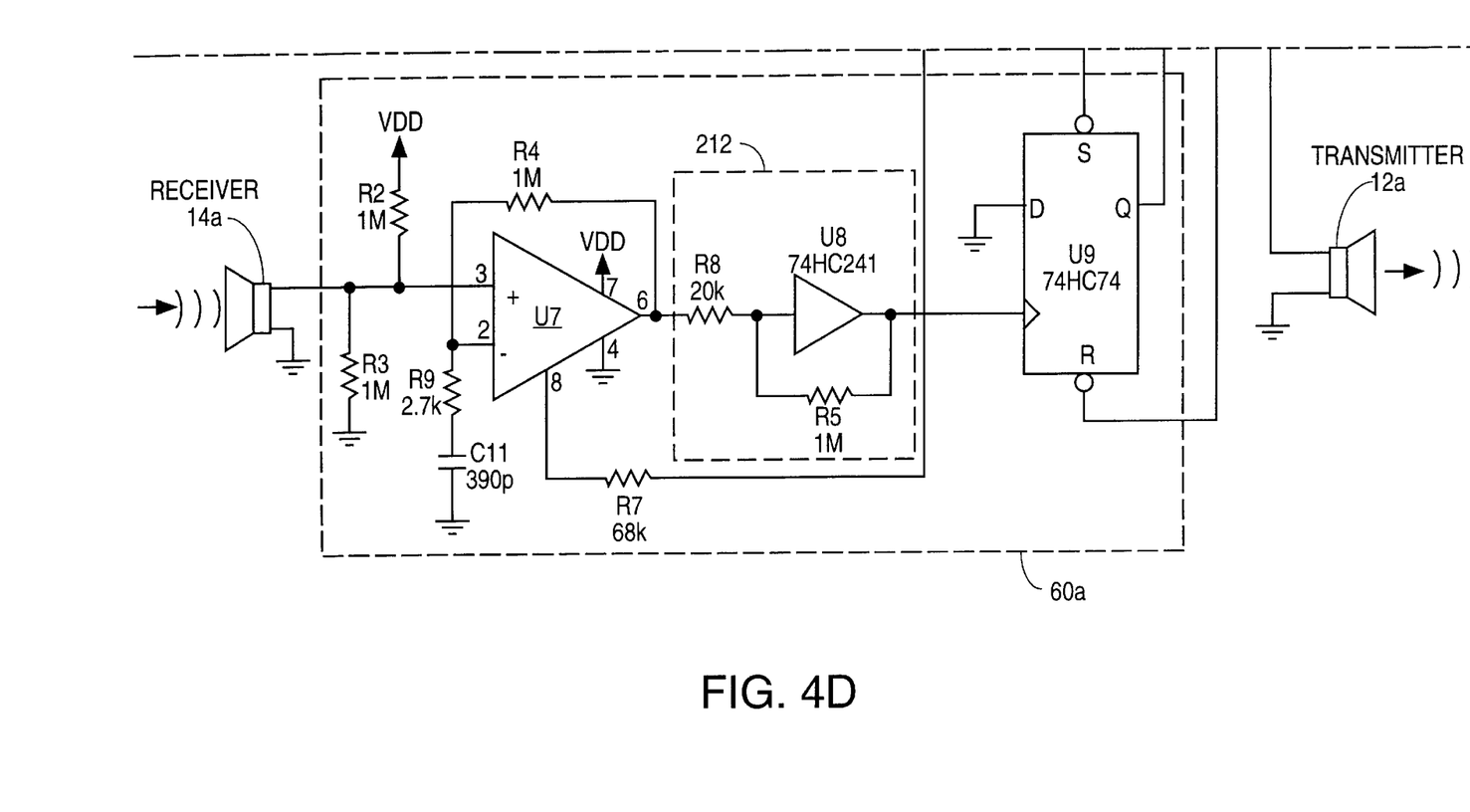

FIG. 4 which consists of FIGS. 4A, 4B, 4C and 4D is a schematic diagram of one embodiment of a personal speedometer in accordance with the present invention. A battery BT1 has its negative terminal coupled to ground and its positive terminal coupled to a voltage source $V_{DD}$ (approximately equal to 3.0 volts). 0.1 picofarad (pF) capacitors C1, C2, C3, C4 and C5 are bypass capacitors coupled in parallel with battery BT1 between ground and $V_{DD}$. The bypass capacitors operate to filter voltage fluctuations.

Controller 16a comprises a controller U1, a 1.0 MHz crystal controlled oscillator circuit 200 and a power on reset circuit 202. Controller U1 is, in one embodiment, an "Hitachi HD68701" complementary metal oxide semiconductor (CMOS) single chip microprocessor having 2 kilobytes of erasable programmable read only memory (EPROM), 128 bytes of random access memory (RAM) and a programmable timer. The built in EPROM and RAM enable controller U1 to store and execute source code such as that contained in APPENDIX 1, which is part of this application and incorporated herein by reference in its entirety. Controller U1 executes the source code contained in APPENDIX 1 to perform the functions described below.

The source code contained in APPENDIX 1 is assembly source code. The assembly source code is run through an assembler which compiles the assembly source code into a machine code file. The machine code file is then loaded into the memory of a microprocessor programmer. The microprocessor programmer then loads the machine code file into the EPROM of controller U1. In alternative embodiments, the machine code file is stored in a ROM (read only memory) inside a microprocessor (controller).

Crystal controlled oscillator circuit 200 comprises a 2.7 kiloohm (KΩ) resistor R1 having a first lead coupled to a lead 204 of controller U1. Coupled to a second lead of resistor R1 is a first lead of a 1.0 MHz crystal CY1 and a first lead of a 22 pF capacitor C6. A second lead of crystal CY1 and a first lead of a 22 pF capacitor C7 is coupled to a lead 206 of controller U1. Second leads of capacitors C6, C7 are coupled to ground. Crystal controlled oscillator circuit 200 provides a 1.0 MHz signal which is used internally by controller U1 as the master clock.

Power on reset circuit 202 includes a 100 KΩ resistor R10 and a 0.1 pF capacitor C8 series connected between voltage source $V_{DD}$ and ground with the node intermediate these two components coupled to a lead 208 of controller U1. Power on reset circuit 202 is required for the proper power on sequence of controller U1.

Zero switch circuit 92a includes a 100 KΩ resistor R9 coupled between a lead 214 of controller U1 and a source of voltage $V_{DD}$ and a switch SW1 coupled between lead 214 and ground. When the user closes switch SW1, the voltage on lead 214 is driven to ground which initiates a measurement cycle as discussed below. When switch SW1 is open, resistor R9 pulls up the voltage on lead 214 to $V_{DD}$.

A thermistor circuit 82a includes a thermistor TR1 having a lead coupled to a lead 216 of controller U1 and an inverting amplifier U11 having an output lead also coupled to lead 216. First leads of a 100 KΩ resistor R12 and a 0.47 pF capacitor C9 are coupled to a second lead of thermistor TR1. A second lead of capacitor C9 and an output lead of an amplifier U10 are coupled to the input lead of inverting amplifier U11. A second lead of resistor R12 is coupled to the input lead of amplifier U10.

Thermistor circuit 82a is an RC oscillator, the frequency of which is dictated by capacitor C9 and thermistor TR1. Since the resistance of thermistor TR1 is dependent upon temperature, the frequency of the signal output by thermistor circuit 82a is also dependent upon temperature. Controller U1 measures the frequency of the signal at lead 216 and hence the frequency of the signal output by thermistor circuit 82a. Controller U1 uses the measured frequency to calculate the current air temperature.

Controller U1 has an output lead 26a coupled to the reset input leads of flip flops 22a, 24a and U9. Output lead 26a is also coupled to an input lead of a counter 44a through an inverting amplifier U6. Controller U1 outputs a reset signal at output lead 26a which clears flip flops 22a, 24a, U9 and counter 44a.

Controller U1 begins a measurement cycle by deasserting the reset signal at output lead 26a and asserting a set signal at an output lead 18a. Output lead 18a is coupled to set input leads of flip flops 22a, 24a and U9. Thus, the set signal sets flip flops 22a, 24a and U9. As a result, logic high signals are output at the Q outputs of flip flops 22a, 24a and U9.

Oscillator circuit 38a includes a NAND gate U5 having a B input lead coupled to the Q output lead of flip flop 24a. The output lead of NAND gate U5 is coupled to a first lead of a 2.7 KΩ resistor R11. A 1.0 megohm (MΩ) resistor R6 and a 10.24 MHz crystal CY2 are coupled in parallel between an A input lead of NAND gate U5 and a second terminal of resistor R11. A 22 pF capacitor C10 is coupled between ground and the second terminal of resistor R11.

When the signal received at input lead B of NAND gate U5 from the Q output lead of flip flop 24a is at logic low, NAND gate U5 is disabled and oscillator 38a does not oscillate. However, when the signal received at input lead B of NAND gate U5 is at logic high, NAND gate U5 is enabled and oscillator 38a oscillates and produces a 10.24 MHz square wave signal which is coupled to clock input leads of flip flops 22a, 24a and also to a clock input lead 210 of counter 44a.

Counter 44a is a multistage ripple counter with stages Q0 to Q7 representing the first stage through the eighth stage, respectively. Counter 44a is coupled by bus 50b to controller U1. The output signal from stage Q7 is also transmitted to an input lead of transmitter 12a.

Since controller U1 is no longer asserting the reset signal at output lead 26a and since clock input lead 210 of counter 44a is receiving a 10.24 MHz signal, counter 44a counts and outputs a 40 KHz signal at the output lead from stage Q7 which is coupled to the input lead of transmitter 12a. Transmitter 12a converts the 40 KHz signal to an ultrasonic sound wave which propagates through a tube (not shown) to an ultrasonic receiver 14a. The output lead of ultrasonic receiver 14a is coupled to the non-inverting input lead of an operational amplifier U7 (op-amp U7) of an amplifier circuit 60a.

Amplifier circuit 60a further includes a 1.0 MΩ resistor R2 coupled between $V_{DD}$ and the non-inverting input lead of op-amp U7 and a 1.0 MΩ resistor R3 coupled between ground and the non-inverting lead of op-amp U7. Resistors R2 and R3 form a voltage divider which DC biases the non-inverting input lead of op-amp U7 at half $V_{DD}$.

The output lead of op-amp U7 is fed back through a 1.0 MΩ resistor R4 to the inverting input lead of op-amp U7. A 390 pF capacitor C11 and 2.7 KΩ resistor R9 are coupled in series between ground and the inverting input lead of op-amp U7. Resistors R4, R9 and capacitor C11 determine the gain of op-amp U7.

To conserve power, an input lead of op-amp U7 is coupled through a 68 KΩ resistor R7 to the QN output lead of flip flop 24a. When the output signal on the QN output lead of flip flop 24a is high, op-amp U7 is powered down which conserves power.

The output lead of op-amp U7 is also coupled to a first lead of a 20 KΩ resistor R8 of a schmitt trigger circuit 212. Schmitt trigger circuit 212 further includes an amplifier U8 and a 1.0 MΩ resistor R5 coupled in parallel between a second lead of resistor R8 and a clock input lead of flip flop U9. Schmitt trigger circuit 212 reduces noise.

The D input lead of flip flop U9 is coupled to ground. The first few cycles of the sound wave received at receiver 14a, will produce a clock input signal at the clock input lead of flip flop U9. However, flip flop U9 does not toggle because controller U1 is still asserting the set signal at output lead 18a. Controller U1 then deasserts the set signal. The next transition of the received sound wave will produce a rising clock edge at the clock input lead of flip flop U9 and as a result the Q output lead of flip flop U9 toggles to output a logic low signal.

The Q output lead of flip flop U9 is coupled to the D input lead of flip flop 22a. The Q output lead of flip flop 22a is coupled to the D input lead of flip flop 24a. Since controller U1 has deasserted the set signal and since the Q output lead of U9 is outputting a logic low signal, flip flops 22a, 24a toggle with the next 10.24 MHz clock signal received from oscillator circuit 38a. This causes a logic low signal to be output on the Q output lead of flip flop 24a which stops oscillator circuit 38a from oscillating. As a result, counter 44a stops counting with a count corresponding to the phase of the sound wave received by receiver 14a.

Controller U1 receives the count information via bus 50b and calculates the air velocity. A two digit liquid crystal display (LCD) 108a is coupled by a bus 104a to controller U1. Controller U1 outputs an output signal on bus 104a representing the air velocity to LCD display 108a, which displays the air velocity.

Referring to FIG. 1, apparatus 8 can be readily used as a personal speedometer, i.e. to accurately measure the air speed of a user.

Figure 5A:
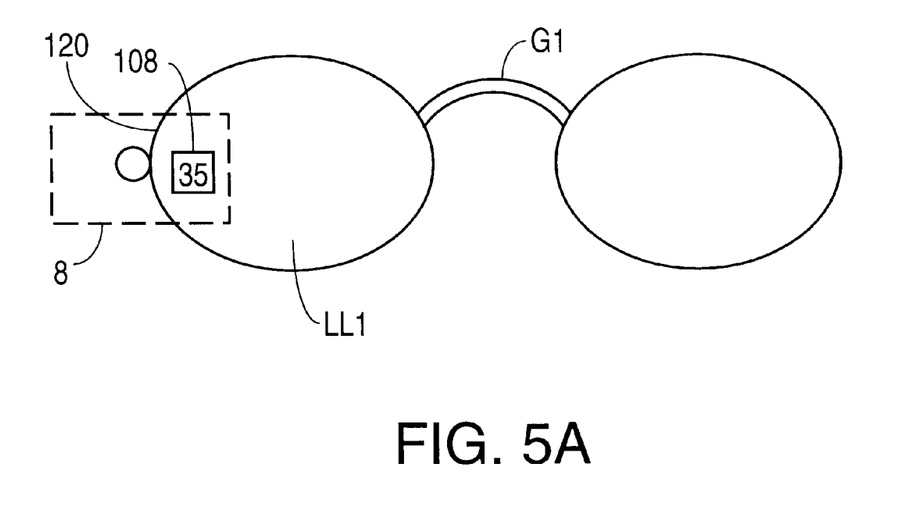
FIGS. 5A and 5B are rear and top views, respectively, of one embodiment of the personal speedometer mounted on glasses in accordance with the present invention.
Figure 5B:
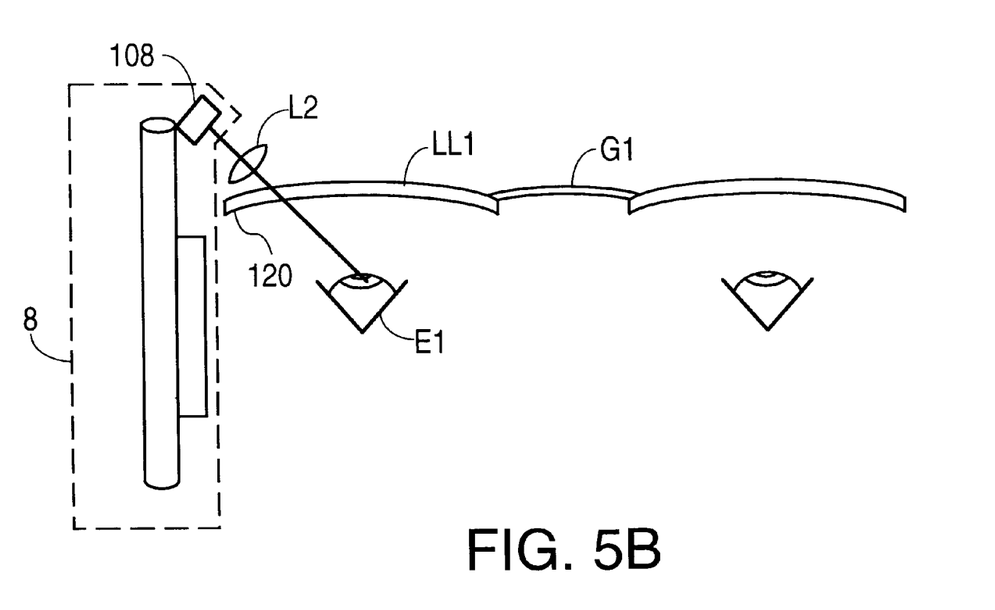

FIGS. 5A and 5B show rear and top views, respectively, of an embodiment of the present invention which includes apparatus 8 mounted on glasses G1. Display 108 is mounted to the left side 120 of the left lens LL1 so as not to block the user's normal field of vision. A magnifying lens L2 is used to bring display 108 into focus and is located between the user's left eye E1 and display 108. Although FIGS. 5A and 5B show apparatus 8 mounted on left lens LL1, apparatus 8 can also be mounted on the right side of the right lens, if desired and appropriate change is made in the location of the display relative to the air tube (i.e. the two are switched).

During operation, the speed V of air flow through tube 10 (which approximately equals the speed of the user through air) is displayed on display 108. The user can read the air speed V by looking to the side and in the direction where the display is mounted. This allows the user to readily read the air speed V without involving the user's hands. The personal speedometer is particularly well suited to applications where ground speed calculations are impractical. Examples include hang gliding, horse back riding, jogging, skating and skiing.

Figure 6:
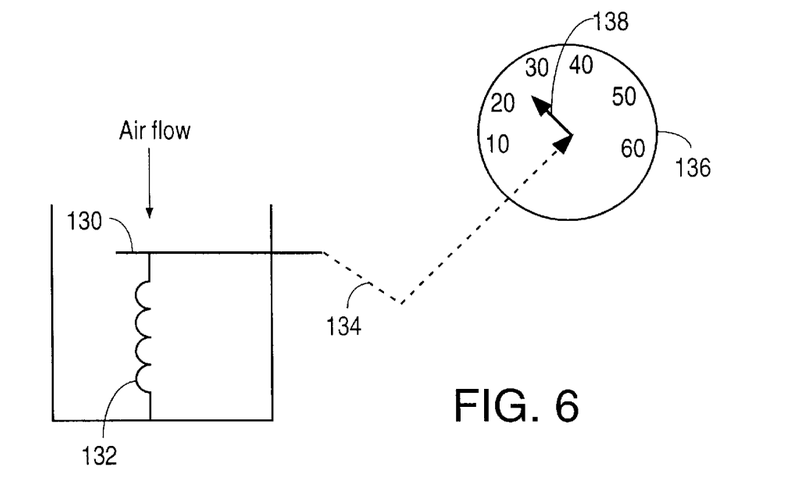
FIG. 6 illustrates an alternative embodiment of a personal speedometer which uses mechanical air resistance to calculate the speed of an object in accordance with the present invention.

An alternative embodiment of the present invention is shown in FIG. 6. As shown, air flows against a plate 130. The air flow against plate 130 causes plate 130 to move and compress spring 132. Mechanical linkage 134 transfers the plate movement to the speed dial 136 such that a needle 138 will move around the face of speed dial 136 proportionally to the force created by air impinging upon plate 130.

The force created by air impinging upon plate 130 is related to the air speed of the object. At higher air speeds, air flow increases and the force exerted on plate 130 correspondingly increases. As the force increases, the displacement of plate 130 increases and mechanical linkage 134 causes needle 138 to move further clockwise around the face of speed dial 136, thus displaying the higher air speed.

Figure 7:
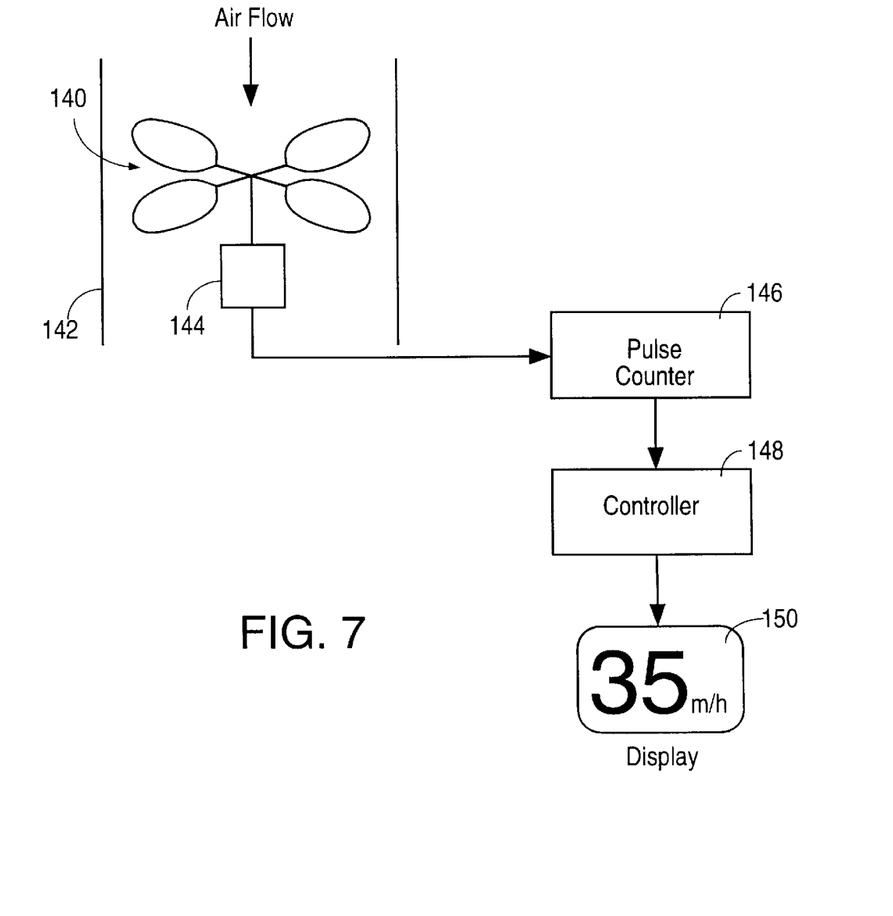
FIG. 7 illustrates an alternative embodiment of a personal speedometer in accordance with the present invention which uses a turbine to determine the speed of an object.

An alternative embodiment of the present invention is shown in FIG. 7. As shown, air flow impinges on a turbine 140, which is mounted in a tube 142. The air flow causes turbine 140 to rotate. Turbine 140 is connected to an electric motor 144 which produces an AC signal with a frequency corresponding to the speed at which turbine 140 rotates. A pulse counter 146 is coupled to motor 144. Pulse counter 146 counts cycles of the signal output by electric motor 144. Pulse counter 146 outputs the cycle count to a controller 148, which is coupled to pulse counter 146. Controller 148 uses the cycle count to calculate the speed of the air flow, and displays the air speed on a display 150, which is coupled to controller 148.

In an alternative embodiment, a satellite global position system (GPS) is used to determine the distance $D_{GPS}$ the object has moved over a fixed period of time $T_{GPS}$. The speed $V_{OBJ}$ of the object is determined from the following equation:

$$V_{OBJ} = D_{GPS}/T_{GPS} \tag{12}$$

Although the present invention has been described with reference to preferred embodiments, persons skilled in the art will recognize that changes may be made in form and detail without departing from the spirit and scope of the invention. For example, the device can be mounted on the user in a variety of ways and at various locations, such as around the user's waist. The device can also be mounted away from the user, for example, the device could be mounted on a hang glider, a ski pole, or on a horse provided the display is still visible to the user. Further, although a 10.2 MHz oscillator is described, other frequency oscillators can be used. Thus the above-described embodiments should be regarded as illustrative rather than restrictive.

I claim:

1. An apparatus for measuring the air speed of an object, said apparatus comprising:

a tube adapted to allow air to flow through;

a transmitter mounted in said tube;

a receiver mounted in said tube a predetermined distance from said transmitter, said receiver adapted to receive sound waves transmitted from said transmitter;

an amplifier having an input lead coupled to an output lead of said receiver, said amplifier adapted to amplify a first signal generated by said receiver from said sound waves;

a flip flop pair having a first input lead coupled to an output lead of said amplifier, said flip flop pair adapted to detect wave transitions of said first signal;

an oscillator having an input lead coupled to an output lead of said flip flop pair, said oscillator generating a second signal at an output lead of said oscillator when said flip flop pair asserts an on-signal at said flip flop pair output lead;

a counter having an input lead coupled to said oscillator output lead, said counter being coupled to said transmitter and said flip flop pair, said counter adapted to count cycles of said second signal;

a controller coupled to said counter, said controller having a first output lead coupled to a second input lead of said flip flop pair, wherein said controller asserts a set-signal on said controller first output lead thereby causing said flip flop pair to assert said on-signal thereby causing said oscillator to generate said second signal, said counter counting cycles of said second signal, and wherein said controller de-asserts said set-signal a predetermined amount of time after said controller asserts said set-signal, thereafter said flip flop pair de-asserts said on-signal upon detecting the next wave transition of said first signal thereby causing said oscillator to stop generating said second signal, said counter stopping with a cycle count indicative of said air speed, said controller adapted to receive said cycle count from said counter;

a display having an input lead coupled to a second output lead of said controller, said display for displaying said air speed; and a zero switch having an output lead coupled to a first input lead of said controller.

2. The apparatus of claim 1 further comprising a thermistor having an output lead coupled to a second input lead of said controller, said thermistor adapted to provide a variable resistance which is related to a temperature of said air.

3. A personal speedometer comprising the apparatus of claim 1 mounted on glasses.

4. The personal speedometer of claim 3 further comprising a magnifying lens for magnifying said display.

5. The apparatus of claim 1 wherein said controller has an input port for receiving said cycle count coupled to an output bus of said counter, said controller calculating said air speed from said cycle count.

6. The apparatus of claim 5 wherein said counter output bus comprises a plurality of channels, one of said channels being coupled to an input lead of said transmitter.

7. The apparatus of claim 1 wherein said predetermined amount of time is greater than or equal to the amount of time for said sound waves to travel from said transmitter to said receiver.

8. The apparatus of claim 7 wherein said tube has a first end and a second end, said predetermined amount of time being less than the amount of time for said sound waves to travel from said transmitter to said first end or said second end of said tube and to said receiver.

* * * * *